United States Patent [19]

Ohshiro

[11] 4,040,413

[45] Aug. 9, 1977

[54] ENDOSCOPE

[75] Inventor: Susumu Ohshiro, Iwatsuki, Japan

[73] Assignee: Fuji Photo Optical Co. Ltd., Omiya, Japan

[21] Appl. No.: 595,425

[22] Filed: July 14, 1975

[30] Foreign Application Priority Data

July 18, 1974 Japan .................................. 49-81739
July 18, 1974 Japan .................................. 49-81740
July 18, 1974 Japan .................................. 49-81741

[51] Int. Cl.$^2$ ............................................. A61B 1/06
[52] U.S. Cl. ..................................... 128/6; 128/2 M; 128/349 B; 128/DIG. 9
[58] Field of Search ........................ 128/4, 6, 7, 8, 11, 128/349 B, 349 BV, 350, 351, 2 M, 244, 344, DIG. 9, DIG. 25

[56] References Cited

U.S. PATENT DOCUMENTS 3,417,745  12/1968  Sheldon ................................. 128/6
3,913,565  10/1975  Kawahara ........................... 128/351

FOREIGN PATENT DOCUMENTS 502,331  3/1939  United Kingdom ...................... 128/8

*Primary Examiner*—Robert W. Michell
*Assistant Examiner*—Henry S. Layton

[57] ABSTRACT

One or more inflatable balloons are provided on the outer surface of the tube of an endoscope which encloses the fiber optical light transmitting bundle. When only one balloon is provided, the balloon is provided on one side of the tube near the end thereof to enlarge the space within a body cavity in one direction and the flexible part of the tube may be bent in said direction. When moe than one balloon is provided, one of the balloons is selectively inflated to enlarge the space within the body cavity in the desired direction. In a preferred embodiment of the invention, the balloons are located at equal intervals around the tube. In another embodiment of the invention, an outer sleeve is provided around the tube with balloons on the outer face thereof and is made slidable with respect to the tube. The outer sleeve and the tube are inserted into the body cavity alternately by alternately inflating the balloons on the outer sleeve and those on the tube to facilitate the insertion thereof into the body cavity.

6 Claims, 6 Drawing Figures

ENDOSCOPE

BACKGROUND OF THE INVENTION

1. Field of the Invention

This invention relates to an endoscope, and more particularly to an endoscope employing a flexible fiber optical light transmitting bundle designed for insertion into inaccessible places, such as the human stomach, intestines etc. for visual examination of these organs.

2. Description of the Prior Art

It has been known in the art to use a flexible fiber optical light transmitting bundle for an endoscope for insertion into inaccessible body cavities. Further, it has also been known to provide an annular balloon around the endoscope some distance back from the rounded tip to stably fix the end of the endoscope within the body cavities and enlarge the field of view of the endoscope.

In the conventional endoscope, however, since the balloon is annular in shape and the flexible part of a light transmitting tube is located at the center of the inflated annular balloon, the angle through which the flexible part of the endoscope can be bent is materially limited and the range of the field of view is also limited to half of the enlarged space within the body cavity.

SUMMARY OF THE INVENTION

In view of the above described defects inherent in the conventional endoscope, it is the primary object of the present invention to provide an endoscope the flexible part of which can be bent through a greater angle in comparison with the conventional endoscope by taking advantage of the whole of the enlarged space within the body cavity.

Another object of the present invention is to provide an endoscope the field of view of which is considerably large in comparison with the conventional endoscopes.

A further object of the present invention is to provide an endoscope which can be easily inserted into the intestines, the duodenum and other body cavities.

A still further object of the present invention is to provide an endoscope which can be inserted deeply into body cavities and which has a field of view which is markedly enlarged so as to enable the observer to see even the orifices of the biliary duct and the pancreatic duct in the duodenum.

The above objects and other objects are accomplished by providing a balloon on one side of the light transmitting tube some distance back from the rounded tip of the endoscope. The number of balloons need not be limited to one but may be as many as three or four. Preferably, three or four balloons are provided around the light transmitting tube and one of the balloons is selectively inflated so that the light transmitting tube within the body cavity need not be rotated in search of the place to be observed. By inflating the balloon on one side of the tube, the flexible part of the endoscope can be bent all the way across the enlarged space within the body cavity and the range of the field of view is markedly enlarged. Thus, it becomes possible to observe even the biliary duct and pancreatic duct, which are very difficult to see with conventional endoscopes. Further, since the field of view is markedly enlarged by the endoscope of this invention, the endoscope can be advanced in the body cavities to observe various parts thereof with fewer stops and starts.

In accordance with another preferred embodiment of this invention, the intermediate body of the endoscope is composed of an inner sleeve including a light transmitting optical fiber bundle and an outer sleeve, said inner sleeve being slidable in said outer sleeve in the longitudinal direction. Both the inner and outer sleeves are provided with balloons therearound and the balloons of the inner sleeve and those of the outer sleeve are inflated and deflated alternately when the endoscope is inserted into the body cavity to facilitate the insertion of the endoscope into the body cavity.

DESCRIPTION OF THE PREFERRED EMBODIMENTS

Figure 1:
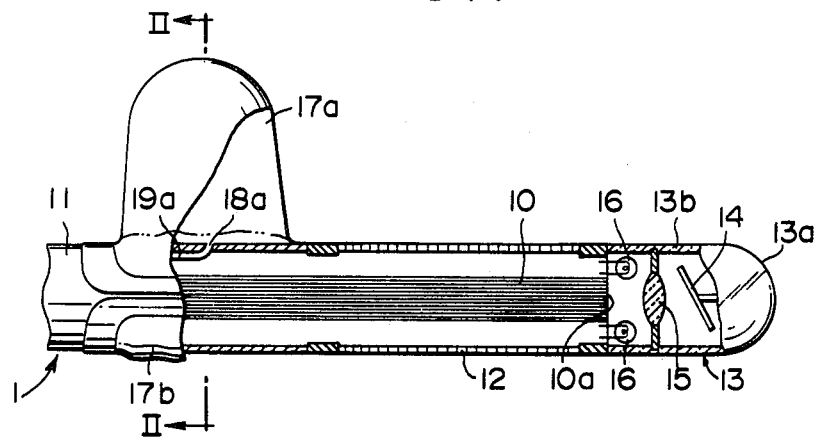
FIG. 1 is a partly sectional longitudinal view showing the end part of the endoscope in accordance with a first embodiment of the present invention.
Figure 2:
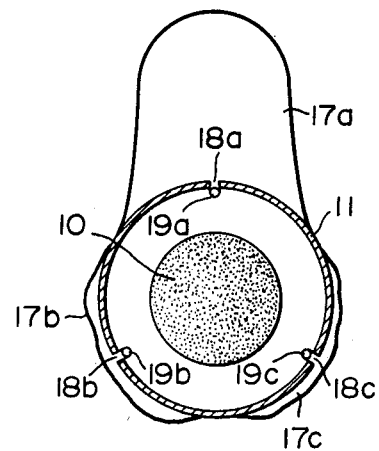
FIG. 2 is a cross sectional view taken along the line II—II of FIG. 1.
Figure 3:
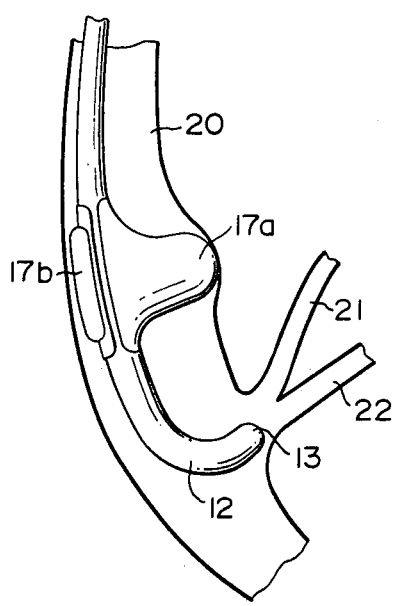
FIG. 3 is a fragmentary side view showing the end part of the endoscope in accordance with the first embodiment of the present invention used for examining internal body organs such as the biliary duct and pancreatic duct.

A first preferred embodiment of this invention is shown in FIGS. 1 to 3, in which only the image taking end part of the endoscope is illustrated. Referring to FIG. 1, a light transmitting tube 1 includes a fiber optical light transmitting bundle 10 extending therethrough. The light transmitting tube 1 is composed of a soft rigid sleeve 11 extending from the operating casing to be located outside the human body (not shown), a flexible sleeve 12 connected with the soft rigid sleeve 11 and a transparent head 13 connected with the flexible sleeve 12 and having a smoothly rounded tip 13a as well known in the art. In the transparent head 13, a rotatable mirror 14 is mounted to the backside of the rounded tip 13a within the head 13a and a focusing lens 15 is located in front of the mirror 14. The fiber optical light transmitting bundle 10 extends through the soft rigid sleeve 11 and the flexible sleeve 12, and the image receiving end face 10a of the bundle 10 faces the focusing lens 15 so that the image of the internal face of the body cavity may be focused thereon. Illuminating lamps 16 are provided in the head 13 adjacent the end face 10a of the light transmitting bundle 10 to illuminate the internal face of a body cavity such as the stomach, the duodenum or the intestines. The light from the illuminating lamps 16 transmits through the transparent wall 13b of the transparent head 13 to illuminate the body cavities. As is well known in the art, wires for remote-controlling the rotatable mirror 14 and lead wires for supplying electricity to the lamps 16 are provided within the tube 1. These are omitted in FIG. 1 for simplification. Further, as is well known in the art, there are provided remote control wires in the tube 1 for bending the flexible sleeve 12 and these are also omitted in the drawing. Around the soft rigid sleeve 11 some distance back from the head 13, are provided three inflatable rubber balloons 17a, 17b and 17c at equal intervals of 120° as shown in FIGS. 1 and 2. At the center of the area on the soft rigid sleeve 11 covered by the balloons 17a, 17b and 17c, there are provided holes 18a, 18b and 18c, respectively. Three air ducts 19a, 19b and 19c communicated at one end with the three holes 18a, 18b and 18c, respectively, are provided on the inner face of the soft rigid sleeve 11. The air ducts 19a, 19b and 19c are communicated at the other end thereof with an air supply source means (not shown) which is capable of supplying air independently to the three air ducts, whereby the three balloons 17a, 17b and 17c are selectively inflated independently of each other. Preferably, the balloons 17a, 17b and 17c are located immediately adjacent to the flexible sleeve 12 so that the body cavity may be expanded at a place as close to the transparent head 13 as possible.

When the endoscope in accordance with the present invention as described above is used, one of the balloons, i.e. 17a for instance, is inflated and the flexible sleeve 12 is bent in the direction of the inflated balloon 17a after insertion of the endoscope into the body cavity up to the place to be observed as shown in FIG. 3. When the balloon 17a is inflated, the light transmitting tube 1 is forced to one side of the body cavity such as the intestinal wall 20 and the wall 20 is expanded to enlarge the space within the intestine and enlarge the field of view of the endoscope. By bending the flexible sleeve 12 all the way across the greatly enlarged space within the intestine, it becomes possible to observe even the biliary duct 21 and a pancreatic duct 22 as shown in FIG. 3. Of the balloons, the one which expands the body cavity in the direction of the place to be observed is selected for inflation. In the above embodiment, the balloon 17a is selected to facilitate the observation of the biliary duct 21 and the pancreatic duct 22.

Since one of the balloons is inflated on one side of the tube 1, the body cavity is expanded in one direction and the tube 1 is forced in the opposite direction and accordingly the flexible part of the endoscope can be bent through a larger angle than can the conventional endoscope which employs an annular balloon. Further, since there are provided a plurality of balloons, i.e. three in the above described embodiment, it is not necessary to rotate the light transmitting tube 1 to expand the body cavity in the direction of the place to be observed. In order to enlarge the body cavity in the desired direction, the one of the plurality of balloons which faces the desired place is simply selected and expanded.

Figure 4:
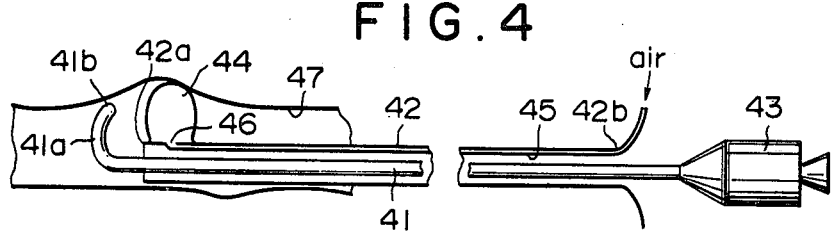
FIG. 4 is a longitudinal view partly in section of the endoscope in accordance with a second embodiment of the present invention showing how the endoscope is used to examine a body cavity.

A second embodiment of the present invention is illustrated in FIG. 4. The endoscope shown in FIG. 4 is comprised of an inner sleeve 41 including a fiber optical light transmitting bundle (not shown) therein and an outer sleeve 42 extending concentrically along the inner sleeve 41. The inner sleeve 41 has a flexible part 41a at one end thereof and is connected with an operating casing 43 at the other end thereof. The flexible part 41a has a smoothly rounded tip 41b at the free end thereof for observation of body cavities as well known in the art. The inner sleeve 41 is slidable lengthwise in the outer sleeve 42. On one side of the outer sleeve 42 adjacent one end thereof 42a near the observation tip 41b is provided an inflatable balloon 44. The balloon 44 is communicated with an air duct 45 which extends from a hole 46 on the outer sleeve 42 within the balloon 44 to the other end 42b of the outer sleeve 42. The air duct 45 is further communicated with an air supply source (not shown) located outside the body.

When the endoscope in accordance with the second embodiment of the invention is used for observing an internal face of a body cavity such as an intestinal wall, the balloon 44 is inflated to enlarge a space within the intestine in one direction and then the flexible part 41a of the inner sleeve 41 is bent in the same direction. Since the balloon 44 is mounted on one side of the outer sleeve 42 of the endoscope, the body cavity is expanded in one direction to make a large space for the flexible part 41a of the inner sleeve 41 to be bent in. Thus, there is obtained a large field of view.

It will be readily understood by those skilled in the art that a plurality of balloons may be provided around the outer sleeve 42 as in said first embodiment so that one of the balloons may be selected and inflated to enlarge the body cavity in the desired direction.

Figure 5:
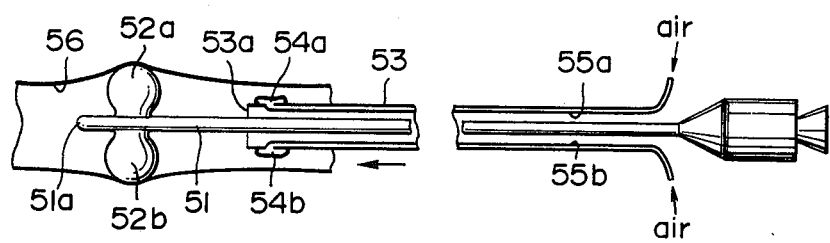
FIGS. 5 and 6 are longitudinal views partly in section of the endoscope in accordance with a third embodiment of the present invention showing how the endoscope is inserted into a body cavity.
Figure 6:
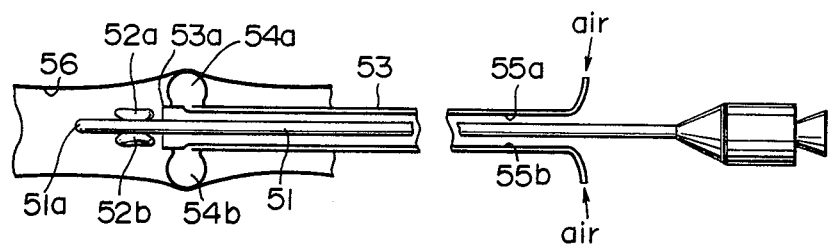

A third embodiment of the endoscope in accordance with the present invention is illustrated in FIGS. 5 and 6 which show different stages of insertion thereof into a body cavity. The endoscope in accordance with this embodiment is composed of an inner sleeve 51 having a rounded tip 51a and a plurality of balloons 52a and 52b on the side thereof some distance back from the rounded tip 51a, and an outer sleeve 53 having a plurality of balloons 54a and 54b on the outer face thereof in the vicinity of an end 53a thereof. The outer sleeve 53 corresponds to the outer sleeve 42 of the second embodiment as shown in FIG. 4 and is also provided with air ducts 55a and 55b communicated with the balloons 54a and 54b, respectively. The balloons 52a and 52b provided on the side of the inner sleeve 51 correspond to the balloons 17a, 17b and 17c of the first embodiment in substance. The balloons 52a, 52b and 54a, 54b are capable of being inflated independently. Therefore, they can be inflated either selectively or simultaneously. The inner sleeve 51 is slidable with respect to the outer sleeve 53.

When the endoscope is inserted in a body cavity, the balloons 52a and 52b of the inner sleeve 51 and the balloons 54a and 54b of the outer sleeve 53 are alternately inflated and deflated and the inner sleeve 51 and the outer sleeve 53 are alternately advanced into the body cavity 56. In more detail, the inner sleeve 51 with deflated balloons 52a and 52b is first inserted into the body cavity 56 up to a position to which the inner sleeve 51 can be inserted comparatively easily. Then, the balloons 52a and 52b provided on the inner sleeve 51 are inflated simultaneously to enlarge the space in the body cavity 56 therearound as shown in FIG. 5. Thus, the insertion of the outer sleeve 53 into the body cavity 56 is facilitated. After the outer sleeve 53 with deflated balloons 54a and 54b has been inserted into the body cavity 56, the balloons 54a and 54b are inflated simultaneously to enlarge the space therearound and the balloons 52a and 52b on the inner sleeve 51 are deflated as shown in FIG. 6. Then, the inner sleeve 51 is further advanced into a deeper part of the body cavity 56. By repeating the above steps, the endoscope can easily be inserted deeply in the body cavity without pain.

When the endoscope has reached the place of the body cavity 56 to be observed, one of the balloons is selectively inflated and the flexible part of the inner sleeve 51 is bent to obtain a large field of view in the body cavity 56.

In the above described third embodiment of the invention as shown in FIGS. 5 and 6, it is possible to easily interchange only the inner sleeve 51 including the fiber optical light transmitting bundle with a different kind of inner sleeve which has a different function from that of the inner sleeve 51.

I claim:

1. An endoscope for visual internal examination of body cavities comprising:
    a light transmitting tube including a fiber optical light transmitting bundle having an image receiving end and an image output end, a sleeve extending around and along the light transmitting bundle concentrically therewith for enclosing the bundle for protection thereof and facilitating the insertion thereof into body cavities, and an image taking head connected with the image receiving side end of the sleeve having therein an optical system for focusing an image of the internal view of the body cavities on the image receiving end of the light transmitting bundle,
    a plurality of inflatable balloons provided on the outer face of said sleeve so as to be inflated radially outwardly in different directions, said balloons being selectively and independently inflated,
    said sleeve being flexible between said image taking head and said balloons,
    a plurality of air ducts communicated with said balloons and extending along the sleeve on the internal surface thereof from the balloon to the output end of the sleeve, and
    air supply source means connected with said plurality of air ducts for independently supplying air into said balloons to inflate said balloons independently of each other.

2. An endoscope as defined in claim 1 wherein said balloons are located at equal intervals around the sleeve at the same distance from the image taking head.

3. An endoscope as defined in claim 1 further comprising an outer sleeve extending concentrically with said sleeve and being slidable lengthwise with respect to said sleeve, a plurality of balloons provided on the outer face of said outer sleeve in the vicinity of the end thereof at the same distance from the end, and air supply means for supplying air into said balloons on the outer sleeve.

4. An endoscope as defined in claim 3 wherein said air supply means is capable of selectively supplying air to said balloons on the outer sleeve.

5. An endoscope as defined in claim 1 wherein said air supply means comprises air supply source means and a plurality of air ducts connected between said balloons and said air supply source means, said air ducts extending along the outer sleeve on the internal surface thereof.

6. An endoscope for visual internal examination of body cavities comprising:
    a light transmitting tube including a fiber optical light transmitting bundle having an image receiving end and an image output end, a sleeve extending around and along the light transmitting bundle concentrically therewith for enclosing the bundle for protection thereof and facilitating the insertion thereof into body cavities, and an image taking head connected with the image receiving side end of the sleeve having therein an optical system for focusing an image of the internal view of the body cavities on the image receiving end of the light transmitting bundle,
    an outer sleeve extending concentrically with the light transmitting tube and slidable with respect thereto,
    a plurality of inflatable balloons provided on the outer face of said outer sleeve so as to be inflated radially outwardly in different directions, said balloons being selectively and independently inflated,
    said sleeve of the light transmitting tube being flexible between said image taking head and a part of the tube covered by said outer sleeve,
    an air supply source means for supplying air for inflating said balloons, and
    an air duct means extending along the outer sleeve on the internal surface thereof from the balloon to the output side end of the outer sleeve to be communicated with said air supply source means for sending air from the air supply source means into said balloons.

* * * * *